United States Patent
Turngren et al.

[11] Patent Number: 5,891,078
[45] Date of Patent: Apr. 6, 1999

[54] STERILE ADHESIVE BANDAGE AND ASSOCIATED METHODS

[76] Inventors: Christina M. Turngren, 339 Chestnut St., St. Paul, Minn. 55102; Dale E. Lanser, W 6016 N. County Trunk A, Elkhart Lake, Wis. 53020; Thomas F. Hilbert, Sr., W 7256 Hunter La., Fondu Lac, Wis. 54937

[21] Appl. No.: 966,604

[22] Filed: Nov. 10, 1997

Related U.S. Application Data

[63] Continuation-in-part of Ser. No. 557,950, Nov. 14, 1995, Pat. No. 5,685,833.

[51] Int. Cl.⁶ ..................................................... A61F 13/00
[52] U.S. Cl. ............................... 602/58; 602/57; 602/900; 604/307; 206/441
[58] Field of Search ................................ 602/41–58, 900, 602/904; 604/307, 308, 180; 206/440, 441

[56] References Cited

U.S. PATENT DOCUMENTS

| | | |
|---|---|---|
| 1,827,354 | 10/1931 | Cooper . |
| 2,005,676 | 6/1935 | Hanover ................................. 206/63.2 |
| 2,133,609 | 10/1938 | Eustis . |
| 2,289,642 | 7/1942 | Flood ..................................... 242/55.2 |
| 2,862,846 | 12/1958 | Blackford et al. . |
| 3,283,886 | 11/1966 | Addis et al. ............................... 206/52 |
| 3,520,403 | 7/1970 | Moshel ................................... 206/63.2 |
| 3,527,342 | 9/1970 | Manzo ..................................... 206/56 |
| 3,530,494 | 9/1970 | Baratta .................................. 206/63.2 |
| 3,531,847 | 10/1970 | Wallerstein ............................... 29/411 |
| 3,835,992 | 9/1974 | Adams, IV ............................. 206/390 |
| 4,161,176 | 7/1979 | Harris, II et al. . |
| 4,600,001 | 7/1986 | Gilman . |
| 4,733,797 | 3/1988 | Haber ......................................... 221/8 |
| 4,807,753 | 2/1989 | Goldstein ................................ 206/390 |
| 4,821,918 | 4/1989 | Turner ....................................... 221/70 |
| 4,830,183 | 5/1989 | Metters ................................... 206/441 |
| 4,867,821 | 9/1989 | Morgan . |
| 4,872,593 | 10/1989 | Behringer ................................ 221/231 |
| 4,884,563 | 12/1989 | Sessions . |
| 4,954,210 | 9/1990 | Desmond ................................. 156/584 |
| 4,993,586 | 2/1991 | Taulbee et al. ............................ 221/25 |
| 5,018,516 | 5/1991 | Gilman . |
| 5,065,894 | 11/1991 | Garland .................................... 221/25 |
| 5,133,477 | 7/1992 | Etheredge, III et al. ................. 221/25 |
| 5,133,821 | 7/1992 | Jensen . |
| 5,160,315 | 11/1992 | Heinecke et al. .......................... 602/57 |
| 5,197,493 | 3/1993 | Grier-Idris ............................. 128/853 |
| 5,271,522 | 12/1993 | Ko et al. .................................. 221/58 |
| 5,336,162 | 8/1994 | Ota et al. .................................. 602/41 |
| 5,501,661 | 3/1996 | Cartmell et al. .......................... 602/58 |
| 5,511,689 | 4/1996 | Frank ....................................... 221/73 |
| 5,531,855 | 7/1996 | Heinecke et al. . |
| 5,685,833 | 11/1997 | Turngren .................................. 602/58 |

Primary Examiner—Jerome W. Donnelly
Assistant Examiner—Kim Lee
Attorney, Agent, or Firm—Nikolai, Mersereau & Dietz, PA

[57] ABSTRACT

A sterile delivery system for delivering an adhesive strip or bandage with one hand. The bandage or strip is encapsulated in a protective sterile covering, whereby the bandage or strip may be removed from its sterile covering and applied with one hand without contaminating any portion of the bandage or strip. The delivery system may be manufactured from suitable thin films and may include a blocking member positioned between the strip and the protective sterile covering. The apparatus and method to manufacture the unique bandage or strip is also disclosed.

22 Claims, 11 Drawing Sheets

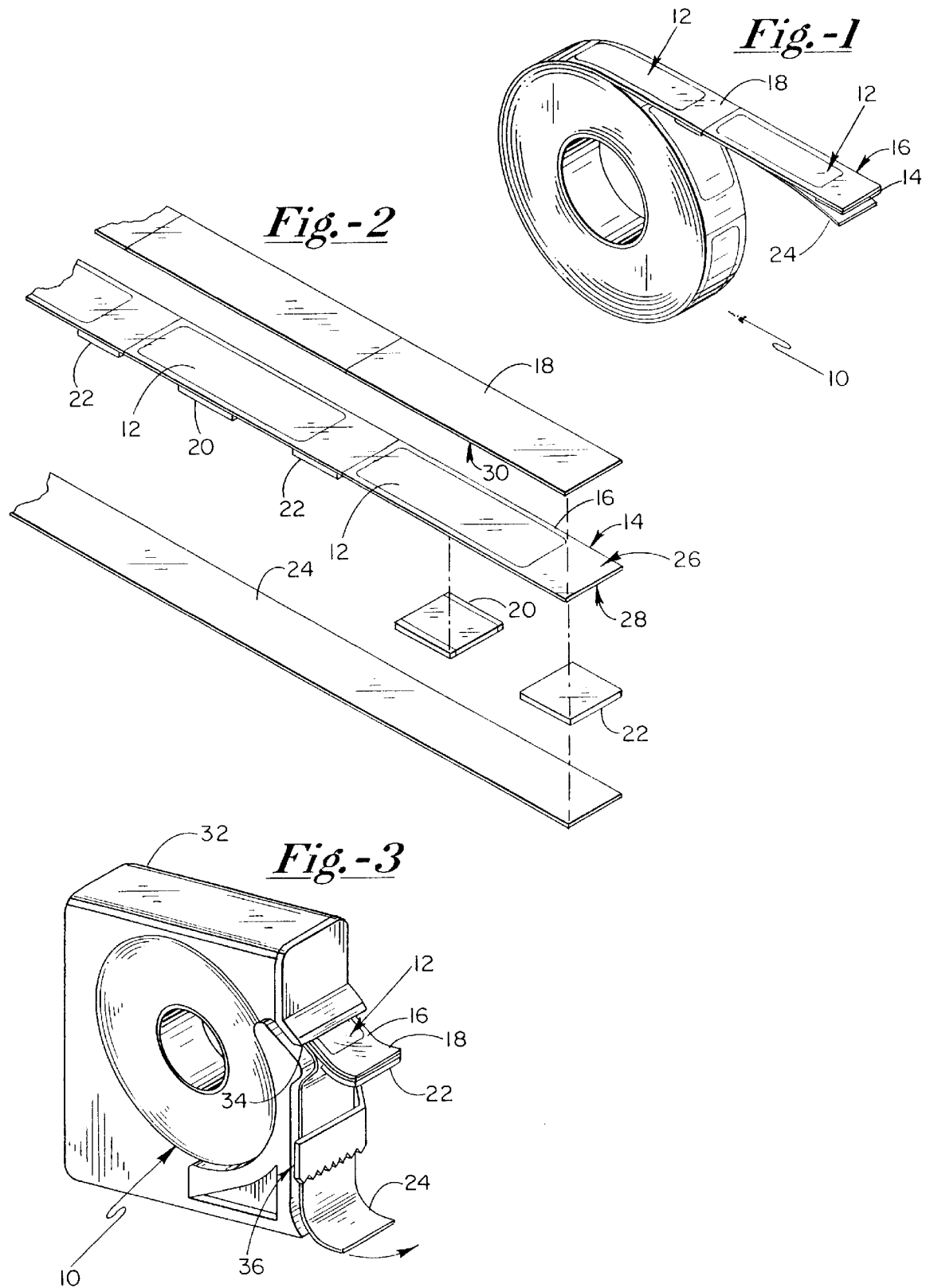

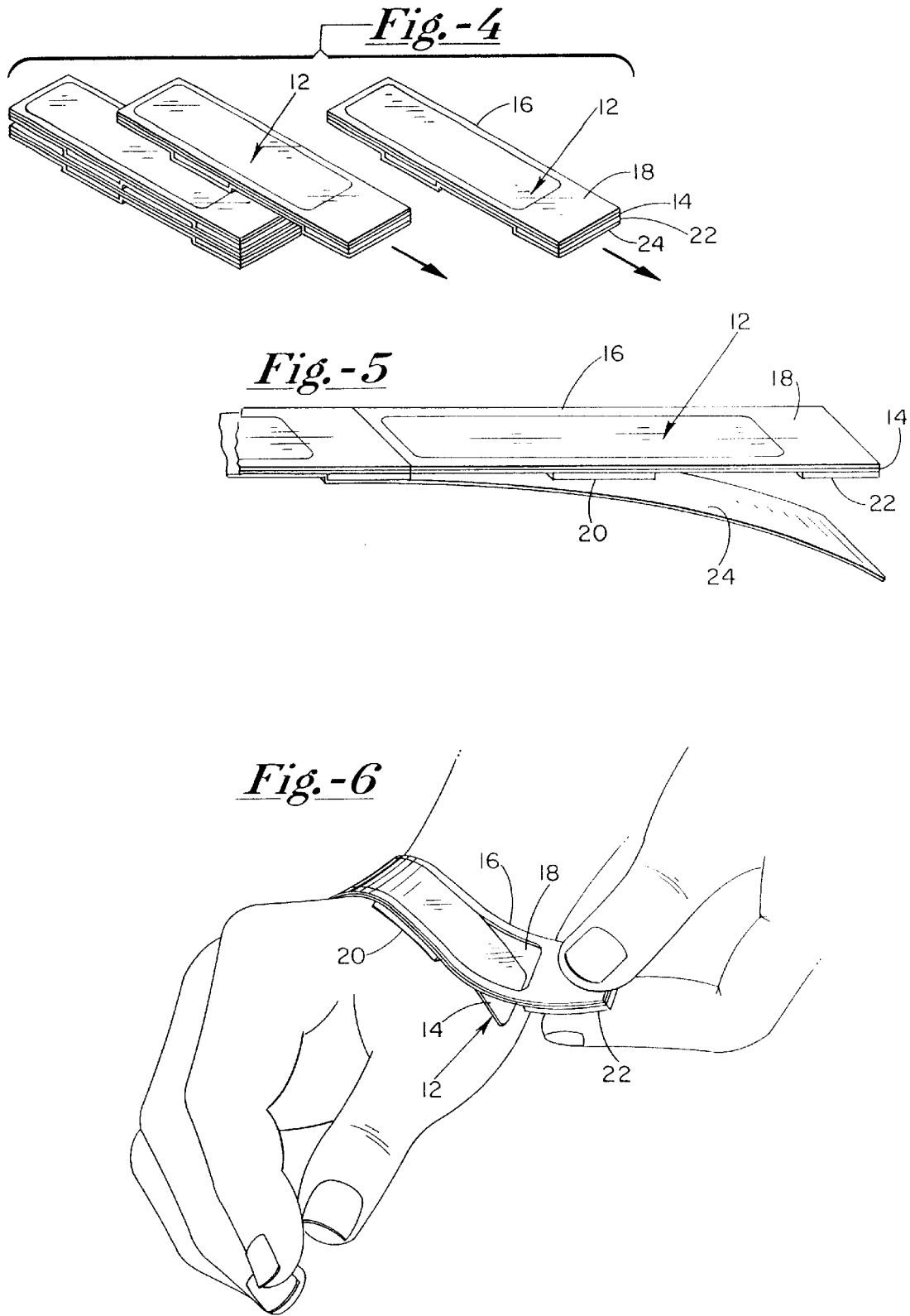

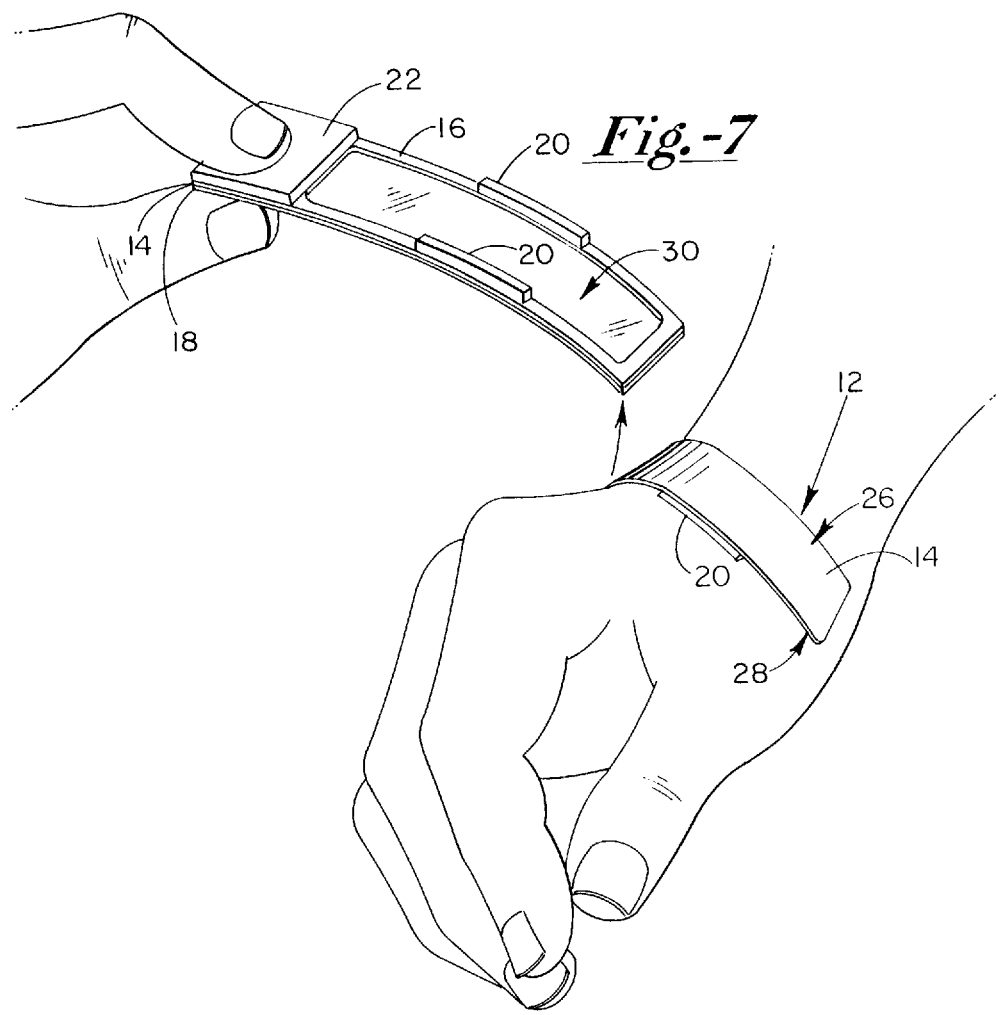
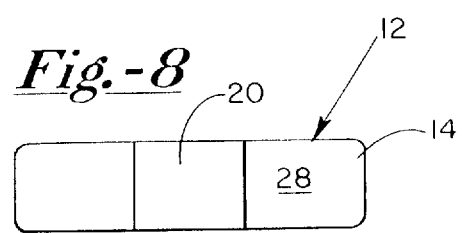

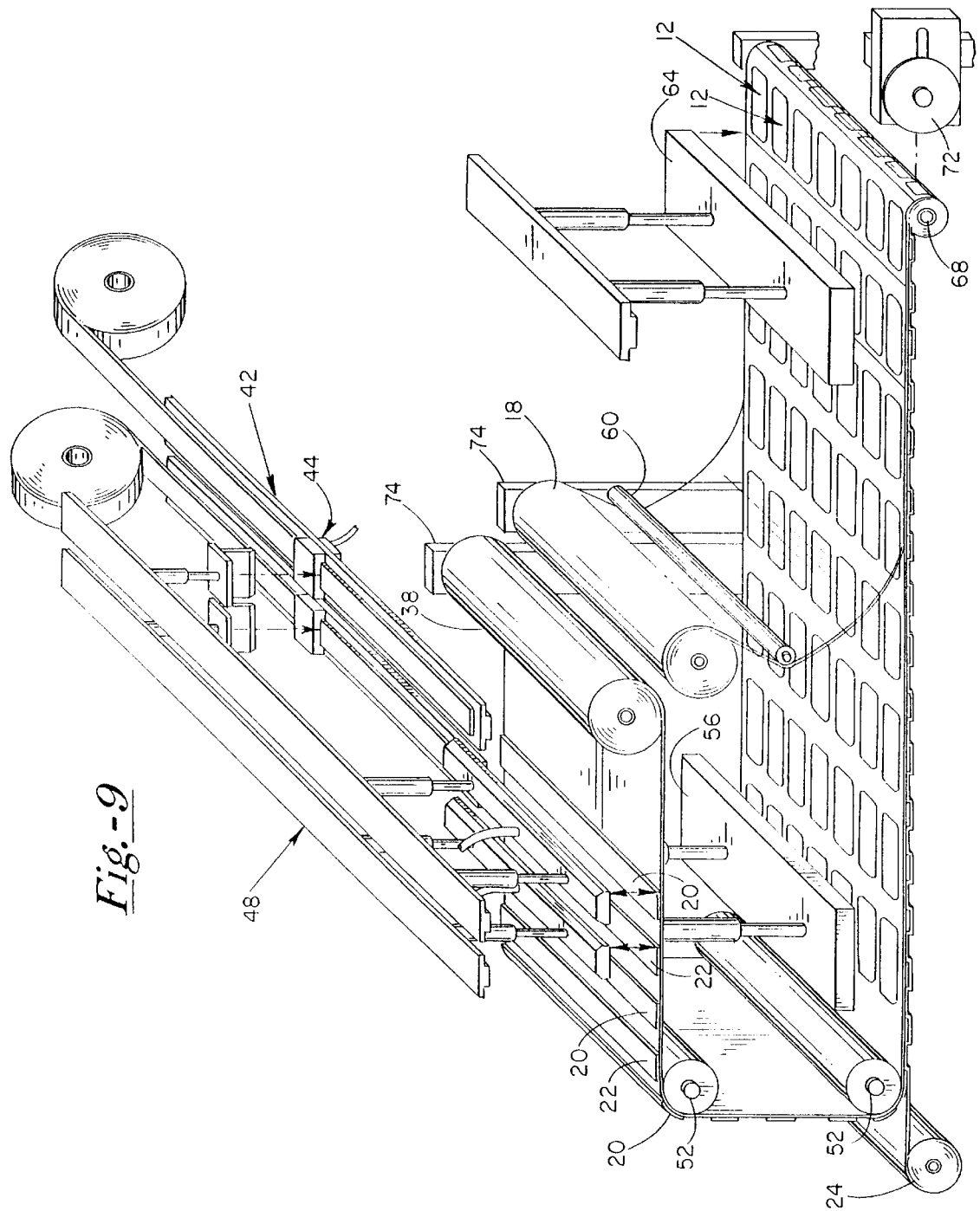

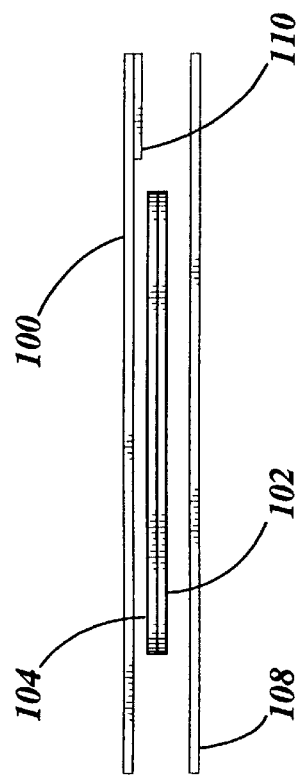
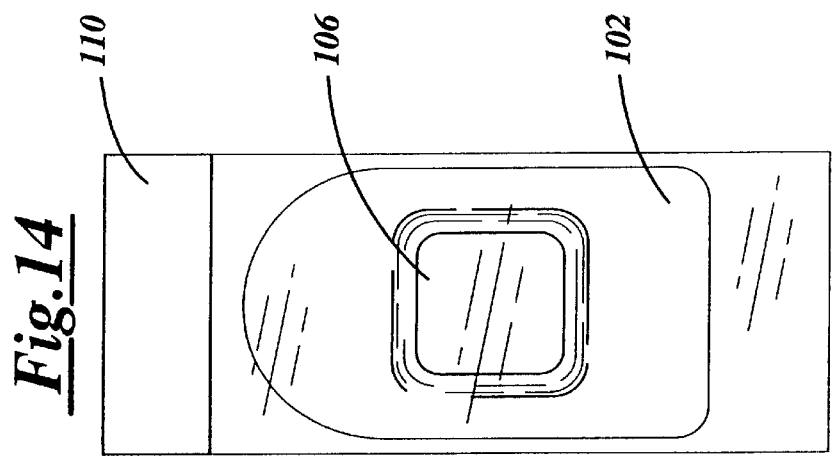

STERILE ADHESIVE BANDAGE AND ASSOCIATED METHODS

CROSS-REFERENCE TO RELATED FILE

The present application is a Continuation-In-Part of application Ser. No. 08/557,950, filed on Nov. 14, 1995, now U.S. Pat. No. 5,685,833, and entitled "STERILE ADHESIVE BANDAGE AND ASSOCIATED METHODS".

BACKGROUND OF THE INVENTION

I. Field of the Invention

This invention relates generally to a sterile delivery system. More particularly, this invention relates to a sterile adhesive bandage or strip, encapsulated in a protective covering, wherein the bandage or strip may be removed from the protective covering and applied with just one hand without contaminating any portion of the adhesive bandage or strip. This invention also relates to the method and apparatus for producing the sterile adhesive bandage or strip contained in the protective covering, wherein the bandages may be dispensed individually or from an interconnected, continuous roll of bandages.

II. Discussion of the Related Art

Over the years, continued refinements have been made to dispensing bandages and other sterile devices. For exemplary purposes, discussion will be directed to the manufacture and application of a commonly packaged sterile adhesive bandage. The conventional bandage includes a gauze or wound pad attached to an adhesive coated strip. Typically, adhesive bandages are contained within sterile packaging that may be assembled as individual packets or an interconnected series. Removing the sterile adhesive bandage from the package typically requires two hands and user contact with either the sterile gauze or a portion of the adhesive strip. This contact either contaminates the gauze pad or reduces the tactile adhesion of the adhesive strip. Protective gloves may be worn during the removal and handling of the sterile bandage, thereby avoiding contamination of the gauze pad, however, the use of sterile gloves is often times neither economical nor efficient and does not avoid the reduction of tactile adhesion when contacting the adhesive strip.

Various delivery systems have been described that assist the user in removing an individual sterile device from its package with only one hand. The following patents describe delivery systems that dispense the sterile device, requiring only one hand by the user: Haber, U.S. Pat. No. 4,733,797 (the '797 patent); Goldstein, U.S. Pat. No. 4,807,753 (the '753 patent); Moshel, U.S. Pat. No. 3,520,403 (the '403 patent); and Cooper U.S. Pat. No. 1,827,354 (the '354 patent). Although these disclosed delivery systems dispense the sterile device, requiring only one hand, the user must use two hands in the later application of the sterile device. Hence, there is a need for a packaged sterile device that may be dispensed and applied with only one hand.

Taulbee, deceased et al., in U.S. Pat. No. 4,993,586 (the '586 patent), and Adams IV, U.S. Pat. No. 3,835,992 (the '992 patent) both disclose an adhesive bandage dispensing package. Taulbee discloses an adhesive bandage sandwiched between an upper and lower protective strip. The adhesive side of the bandage is mounted facing downward on the lower protective strip. One end of the adhesive strip preferably attaches to a mounting pad. The mounting pad facilitates removal of the bandage from the lower protective strip, however, two hands are required to remove the mounting pad from the adhesive strip, and a portion of the sterile bandage must be contacted by the user. Therefore, a need exists for a sterile device, such as a bandage that may be dispensed and applied with one hand without contaminating any portion of the sterile device. Adams, IV, discloses a bandage dispensing package similar to Taulbee et al., which dispenses a bandage from a continuous roll. A mounting pad similar to that described by Taulbee et al. separates one end of the adhesive strips from the lower protective strip. In use, the user must use two hands to separate the mounting pad from the adhesive strip.

Heinecke et al. in U.S. Pat. No. 5,160,315 discloses a combined adhesive strip and transparent dressing delivery system. As shown in FIG. 1 the adhesive strip 22 is applied to the outside of a carrier 18 and 20. Apparently, the adhesive strip is removed from the carriers and then is later applied to a transparent backing 12 as shown in FIGS. 2a–2d. Similar to the prior devices, the Heinecke et al. system requires two hands for the removal and application. Hence, there is a need for a bandage that may be dispensed and applied with only one hand.

Gilman in U.S. Pat. Nos. 5,018,516 and 4,600,001 discloses a wound dressing sandwiched between upper and lower layers of film. Although Gilman in the '001 patent describes his invention as providing "for sterility of the wound dressing layer during application", the wound dressing, lower and upper layers must be packaged in an additional enclosure to maintain sterility. The additional enclosure may increase manufacturing costs, is cumbersome, and requires additional prep time to remove the packaged wound dressing from the additional enclosure. Also, apparently the removal from the enclosure and application of the wound dressing requires two hands. Hence, a need exists for a sterile delivery system enclosing a sterile device in a single enclosure, wherein the sterile device may be dispensed and applied with only one hand. The present invention overcomes these and other disadvantages.

SUMMARY OF THE INVENTION

The purpose of the present invention is to provide a sterile delivery device having an adhesive bandage or strip that may be applied without contaminating any portion thereof. In the preferred embodiment, the bandage or strip can be removed from its sealed sterile package and applied to a desired surface with only one hand without contaminating the tactile adhesive on the strip or bandage. The sterile package, including the bandage or strip, comprises a flexible strip, a carrier member, at least one pull tab, a release backing, and a wound pad (if desired).

The flexible strip has a coating of adhesive deposited on at least the lower planar surface of the strip. The wound pad may be attached to the lower planar surface of the strip and centered such that a portion of the adhesive strip extends from each end of the wound pad. The wound pad and strip are die cut in a predetermined shape, thereby separating the wound pad and strip into an outer surrounding frame and inner bandage. The pull tab is attached to the lower planar surface of the carrier member (or outer surrounding frame when present), proximate an end of the flexible strip.

The flexible strip, wound pad, and pull tab are sandwiched between a carrier member and a release backing. During the manufacturing process, the outer surrounding frame may be removed before the inner strip, wound pad (if present), and pull tab are sandwiched between the carrier member and release backing. The carrier member has a light tack adhesive, thereby attaching to an upper surface of both the inner adhesive strip and outer surrounding frame (if present).

The release backing adheres to the adhesive formed on the lower surface of the flexible adhesive strip, and also adheres to the light tack adhesive on the exposed portion of the carrier member.

Alternatively, the carrier member has a tab attached to each end of the carrier member. The bandage is positioned between the carrier member and release backing with the adhesive side of the bandage contacting the release backing, wherein at least one end of the bandage or strip overlaps a corresponding first tab. The corresponding tab has a portion of its exposed surface coated with an adhesive. The adhesive on the tab holds the bandage to the carrier member as the release backing is removed by pulling the first tab away from the release backing. Once the release backing is removed, the bandage is applied to the desired surface. After the bandage is applied to the desired surface, in order to remove the carrier member the user pulls the second tab away from the bandage, thereby separating the bandage and carrier member. The carrier member has a light tack adhesive coated on the lower surface of the carrier member, wherein the carrier member separates from the bandage when the bandage adheres to the desired surface.

In an alternate embodiment, a plurality of bandages or strips and outer surrounding frames, each having a carrier member attached thereto, are attached in series to a continuous roll of release backing. In use, the bandages or strips may be individually dispensed from the roll. As each bandage or strip is dispensed, the bandage or strip, outer frame (if present) and carrier member separate from the release backing. The user may then center the wound pad or strip over the desired location and press the tab and an adjacent portion of the adhesive strip against the desired surface. The remaining portion of the adhesive strip is pressed against the desired surface. By holding onto the pull tab, the user avoids contaminating contact with the bandage or strip, contaminating contact with the adhesive tactile on the strip, or cross-contamination of the upper surface of the bandage. The pull tab may then be pulled away from the surface, separating the pull tab, carrier and outer frame (if present) from the bandage or strip, leaving the bandage or strip affixed to the desired surface. In this manner, only one hand is required to dispense and apply the bandage or strip to the desired surface.

During the manufacture of the continuous roll of adhesive strips or bandages, a thin film coated with an adhesive may be used to form in rows and columns a plurality of interconnected bandages or strips. The columns of bandages or strips formed on the sheet may be separated, to thereby form a plurality of continuous rolls. In the alternative, the columns and rows of bandages or strips may be divided to form a plurality of individually packaged bandages or strips. Thus, each bandage or strip and outer frame are attached to an independent release backing. A plurality of these bandages or strips may be indexed and dispensed independently. The pull tab may only adhere to the carrier member and is easily separated from the release backing, thereby allowing the user to easily remove the release backing from the carrier member, bandage or strip, and outer frame (if present).

In another alternate embodiment, the flexible strip is constructed of a litmus paper, thereby eliminating the need for a wound pad. The litmus paper may be removed from its package in a manner similar to the removal of the bandage, thereby avoiding any contaminating contact to the paper.

The strip or bandage may be manufactured from a vinyl, woven fabric, non-woven fabric, thin film, urethane, polyester, or other suitable polymer film. Without any limitation intended, when the strip or bandage is manufactured from a urethane, polyurethane, or other thin film, the sterile delivery device preferably includes an adhesive strip, carrier member, at least one tab, a release backing, and a blocking member. The blocking member is sandwiched between the carrier member and adhesive strip. The blocking member has an adhesive layer having a tactile less than that of the carrier member, allowing easy removal of the adhesive strip from the blocking member, wherein the blocking member remains attached to the carrier member. Also, the blocking member is constructed of a slightly thicker and stiffer material than the adhesive strip and carrier, thereby preventing curling of the thin film and carrier.

OBJECTS

It is accordingly a principal object of the present invention to provide a sterile delivery device including an external packaging, whereby a sterile adhesive thin film, strip or bandage may be removed from the external package and applied with a single hand without any contaminating contact to the adhesive strip.

Another object of the present invention is to provide a packaged sterile litmus paper that may be removed from its package without any contaminating contact to the litmus strip.

Still a further object of the present invention is to provide a method of manufacturing a sterile bandage that may be dispensed and applied by the user without contaminating the bandage.

Still another object of the present invention is to provide a method for manufacturing a continuous roll of interconnected bandages that may be separated individually, dispensed, and applied by the user using only one hand.

Still a further object of the present invention is to provide a method of simultaneously manufacturing from a web sheet of thin film, a plurality of continuous rolls of adhesive bandages or strips.

Yet another object of the present invention is to provide a thin film sterile delivery system having a reinforcing member that prevents curling of the device during the application of the thin film.

These and other objects, as well as these and other features and advantages of the present invention will become readily apparent to those skilled in the art from a review of the following detailed description of the preferred embodiment in conjunction with the accompanying claims and drawings in which like numerals in the several views refer to corresponding parts.

DESCRIPTION OF THE DRAWINGS

FIG. 1 is a perspective view of a plurality of interconnected bandages, forming a continuous roll of bandages;

FIG. 2 is a partial exploded perspective view of interconnected bandages;

FIG. 3 is a perspective view of a continuous roll of bandages of the type shown in FIG. 1 being dispensed;

FIG. 4 is a perspective view of a plurality of individual indexed bandages;

FIG. 5 is an enlarged partial perspective view of interconnected bandages having the release backing partially removed;

FIG. 6 is a perspective view of an individual bandage being applied to a patient's wrist;

FIG. 7 is a perspective view of an individual bandage applied to a user's wrist;

FIG. 8 is a bottom plan view of an inner bandage removed from the outer surrounding frame and carrier member;

FIG. 9 is a perspective view, partially in block, of the apparatus for manufacturing the bandage and its package;

FIG. 14 is a top plan view of an of an individually packaged bandage having a transparent carrier member;

FIG. 15 is a partially exploded side elevational view of an adhesive strip and blocker sandwiched between a carrier member and release backing;

DETAILED DESCRIPTION OF THE PREFERRED EMBODIMENT

Figure 10:
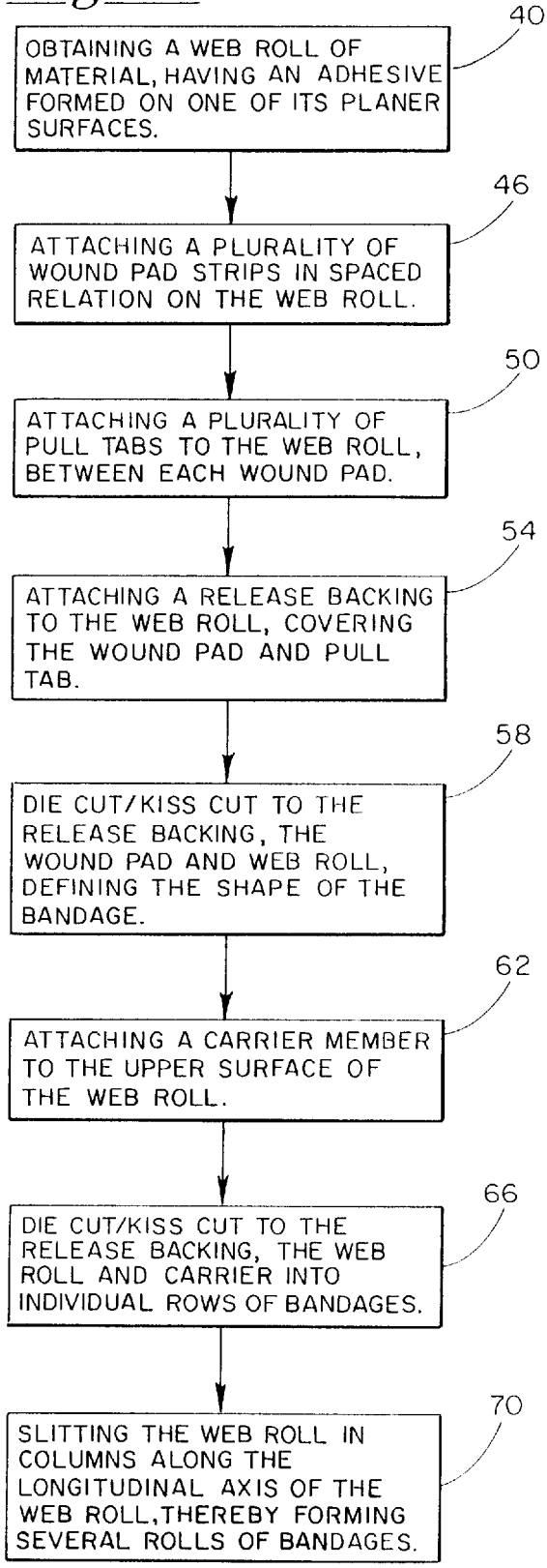
FIG. 10 is a flow diagram of the steps necessary to manufacture a plurality of continuous rolls of bandage rolls of the type shown in FIG. 1.
Figure 11:
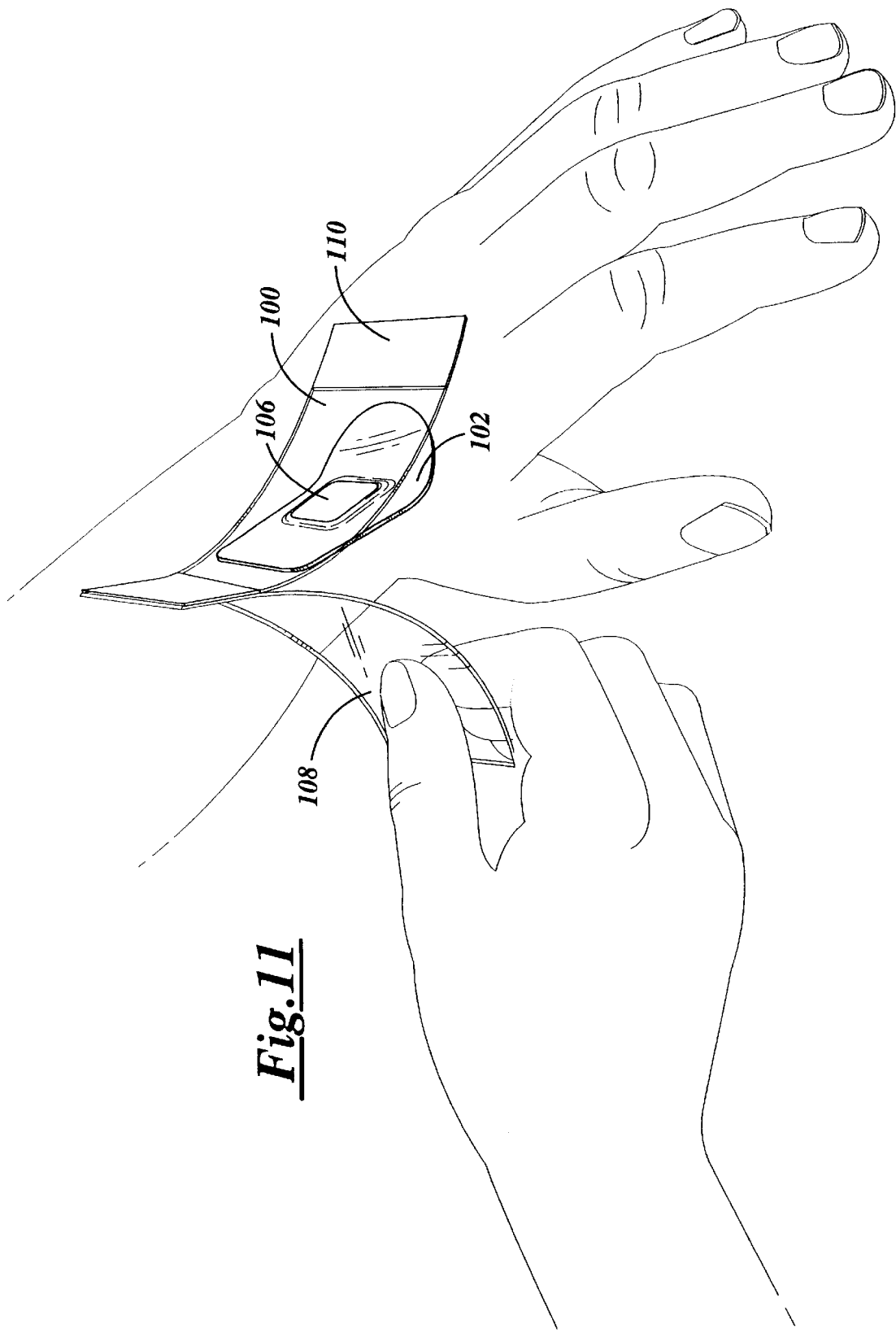
FIG. 11 is a perspective view of an individual bandage being applied to a wrist using just one hand, wherein a tab is affixed on each end of the carrier member.
Figure 13:
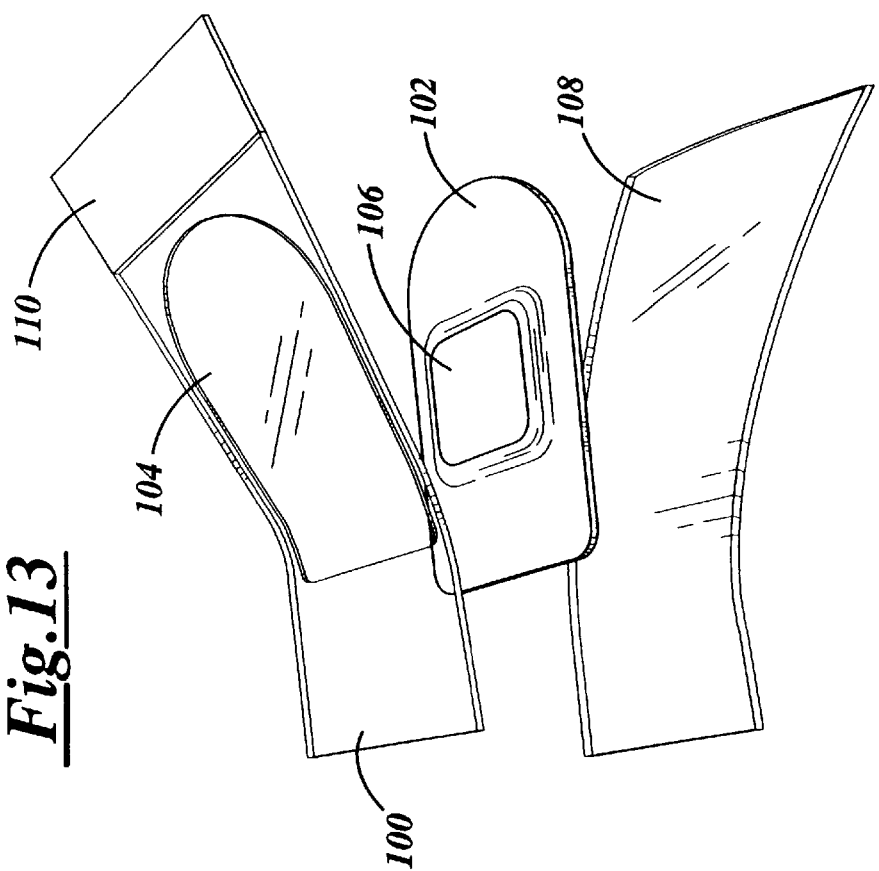
FIG. 13 is a partial exploded perspective view of an individually packaged bandage.
Figure 12:
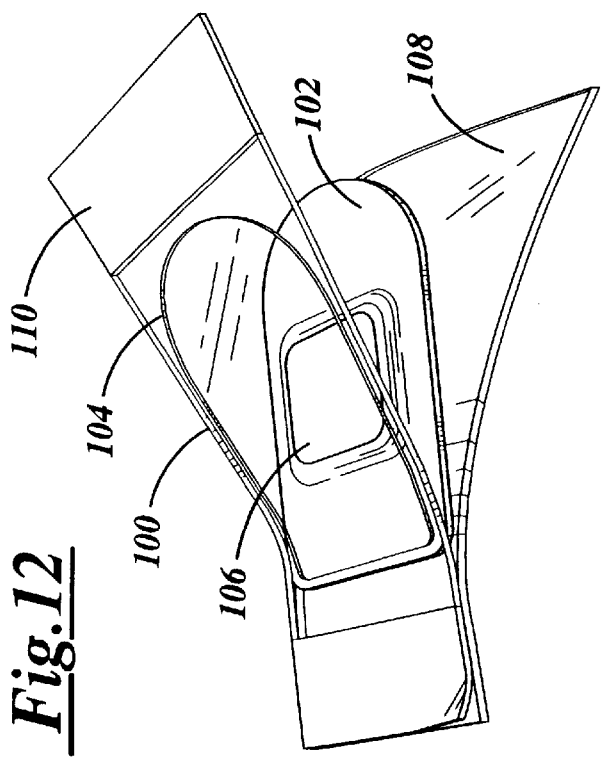
FIG. 12 is a partial perspective view of interconnected bandages having the release backing and carrier member partially separated for clarity.

The sterile delivery system or design of the present invention is generally applicable to medical dressings and is characterized by a sterile adhesive strip interposed and sealed between a carrier member and a release backing, whereby the sterile adhesive strip may be removed from the release backing and carrier member and applied to a desired surface with only one hand. It will be appreciated that the sterile adhesive strip is completely contained between carrier and release backing, thereby eliminating the need for additional sterile packaging. It is further contemplated that various embodiments of the present invention may utilize different materials to produce the sterile adhesive strip, while the materials used to produce the carrier and release backing may remain the same. Also, additional features including multiple tabs and blocking members may be added to the various embodiments to assist in the delivery of the sterile adhesive strip. In accordance with the drawings, several embodiments will now be described in detail.

Referring first to FIGS. 1 and 2, there is shown generally the sterile delivery device 10 of the present invention formed as a continuous roll of bandages 12. Each bandage 12 consists generally of a flexible adhesive strip 14, an outer surrounding frame 16, a carrier member 18, a wound pad 20, a pull tab 22, and a release backing 24. The wound pad 20 and pull tab 22 are attached to the lower planar surface 28 of the adhesive strip 14 (see FIGS. 2 and 8). The bandage 12 is die cut from the adhesive strip 14 and separated from the outer surrounding frame 16. A carrier member 18 is attached to the upper planar surface 26 of the bandage 12 and outer surrounding frame 16. For illustrative purposes, the die cut defining the shape of the bandage 12 is depicted as visible through the carrier member 18. Those skilled in the art will recognize that the carrier member may be manufactured from either an opaque or transparent material of known suitable construction. The lower planar surface 28 of the bandage 12 and outer surrounding frame 16 are shown attached to a continuous roll of release backing 24, thereby forming a continuous roll of interconnected bandages 12.

The flexible strip 14 has an adhesive suitable for medical applications bonded, coated, formed, or otherwise affixed to the lower planar surface 28 of the strip 14. Without limitation, the flexible strip 14 may be of a transparent or opaque: vinyl, woven fabric, non-woven fabric, thin film, urethane, polyester, or other material of suitable known construction. An adhesive may be formed on the upper surface 26 of the flexible strip 14 or the lower surface 30 of the carrier member 18. In the preferred embodiment, a low tactile adhesive is bonded to the lower surface 30 of the carrier member 18. The adhesive is formulated so that when the bandage 12 is removed from the carrier member 18, the adhesive remains on the carrier member 18. Without limitation, this adhesive is a nontransferable light tack adhesive commonly known in the industry as high tack/low tack adhesive, and is available from Minnesota Mining and Manufacturing, Inc., St. Paul, Minn. Without any limitation intended, the release backing 24 is preferably manufactured from a polymer, easily removable from the flexible strip's adhesive. Also, the carrier member is preferably manufactured from a transparent polymer film.

The pull tab 22 does not adhere to the release backing 24, allowing the user to easily separate an end of the release backing and carrier member 18 and remove the release backing from an individual bandage 12. When the bandage 12 and outer surrounding frame 16 are sandwiched between the carrier member 18 and the release backing 24, an air tight seal is formed, whereby the wound pad 20 and bandage 12 remain sterile. If the surrounding frame 16 is removed during the manufacturing process, a portion of the carrier member 18 and release backing 24 overlap the bandage, such that an outer portion of the carrier member and release backing engage each other and form the air tight seal.

Referring next to FIG. 3, a continuous roll of bandages 12 is positioned within a dispenser 32, whereby each bandage 12 may be dispensed with only one hand. The bandage 12 is shown partially dispensed. As the user pulls on the pull tab 22, the bandage 12, outer surrounding frame 16, and carrier member 18, together, exit an opening in the dispenser while the release backing 24 separates from the flexible adhesive strip 14 and is guided away through a guide channel 36. Each bandage 12, outer surrounding frame 16 and carrier member 18 are separated from the continuous roll in a similar fashion.

An alternate preferred embodiment of the delivery device is shown in FIG. 4. Each bandage 12 and outer frame 16 are shown attached to an independent strip of release backing 24. A plurality of bandages 12 are shown indexed and may be dispensed independently, whereby the arrows aligned with the longitudinal axis of the bandage 12 indicate the dispensing motion and direction. When the user dispenses an individually indexed bandage 12, the pull tab 22 assists the user in easily removing the release backing 24 from the bandage 12, outer frame 16 (if present) and/or carrier member 18.

FIGS. 5–7 further illustrate how the bandage 12 is separated from the release backing 24, carrier member 18 and outer frame 16. The release backing 24 is first removed from the lower planar surface 28 of the bandage 12 and outer surrounding frame 16 (see FIG. 5). The user then aligns the wound pad 20 over the desired surface and presses the adhesive strip 14 against the desired surface. The user then pulls the pull tab 22 away from the desired surface, towards the other end of the adhesive strip 14. The difference in tactile between the adhesive on the carrier member 18 and on the strip 14 allows the bandage 12 to separate from the carrier member 18, while adhering to the desired surface. The outer surrounding frame 16 (if present) remains attached to the carrier member 18, when the pull tab 22 is used to peel the outer frame 16 and carrier member 18 from the desired surface. In this manner only one hand is required to dispense and apply the bandage 12 to a desired surface.

Figure 18:
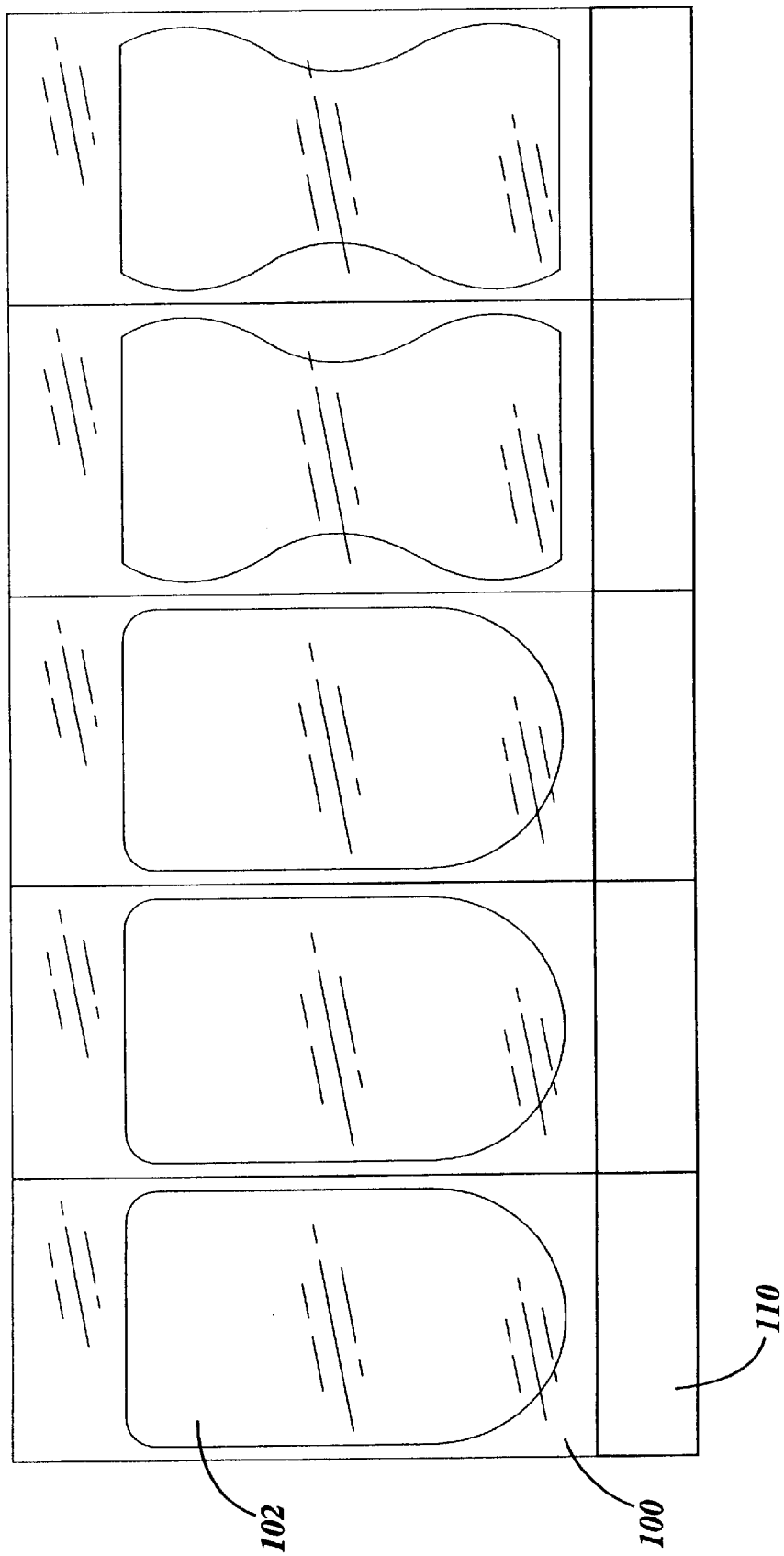
FIG. 18 is top plan view of a plurality of interconnected sterile delivery devices.

Referring next to FIGS. 9 and 10, an apparatus for manufacturing a plurality of continuous rolls of bandages or strips is generally shown and described. The apparatus includes several stations that perform various functions on a thin film adhesive strip 14 or web roll 38 being continuously fed therethrough, thereby forming continuous rolls of bandages or strips. After obtaining a thin film sheet or web roll 38 of material having adhesive deposited on at least one planar surface (see block 40), the continuous web roll 38 is fed past a first station 42, wherein a vacuum placing system 44, of known construction, systematically places strips of wound pad 20 in spaced relation on the adhesive surface of the web roll 38 (see block 46). Without any limitation intended, the bandages may be oriented such that a continuous roll of wound pad may be applied to the web roll 38 (see FIG. 18). In an alternate preferred embodiment, individual wound pads 20 are systematically placed on the adhesive surface of the web roll 38 and arranged in island placement. When the wound pad 20 is arranged on the web by island placement, a portion of the adhesive strip extends from the wound pad 20 from all sides of the wound pad.

Those skilled in the art will appreciate that the step of applying wound pads 20 may be omitted, thereby producing a sterile adhesive strip 14 enclosed by the release backing 24 and carrier member 18. The web roll 38 continues forward to a second station 48, where strips of pull tab 22 are systematically positioned and attached to the web roll 38. The pull tab 22 is positioned on the web roll 38 a predetermined distance from each wound pad 20 or a predetermined distance from an end of each adhesive strip 14 (see block 50). Of course, an additional pull tab 22 may be attached and positioned a predetermined distance from each wound pad 20 or end, such that a pull tab 22 will be attached at each end of the adhesive strip 14.

Those skilled in the art will recognize that the vacuum placing system 44 may either simultaneously or individually place the wound pad 20 and pull tab 22 on the adhesive surface of the web roll 38. The vacuum placing system as shown, has two independent vacuum plates of known construction, however, those skilled in the art will recognize that one vacuum plate may be used to place the wound pad 20 and pull tab 22 on the adhesive surface of the web roll 38 in spaced relation, either simultaneously or independently. Alternatively, the bandages or strips may be oriented such that continuous rolls of tabbing and wound pads may be aligned and applied to the web roll 38.

Guide rollers 52 direct the web roll 38 over a sheet roll of release backing 24, whereby the release backing 24 is pressed against the lower adhesive surface of the adhesive strip 14 or web roll 38. The release backing 24 is thereby attached to the web roll 38, sealably covering a the wound pad 20 and pull tab 22 between the release backing and adhesive strip (see block 54). A first die 56 of known construction having a predetermined shape die cut/kiss cuts through the wound pad 20 and web roll 38 but short of the release backing to thereby form a plurality of bandages having predetermined shapes (see block 58). The planar outer surrounding frame and inner strip are thus defined. Those skilled in the art will appreciate that once the web is die cut/kiss cut, the web may be directed away from the release backing thereby removing the outer surrounding frame and leaving the plurality of inner adhesive strips affixed to the sheet of release backing.

The sheet or roll of carrier member 18 is then guided into contact with the web roll 38 (if present) and overlapping portions of the release backing 24 (if any) by guide roller 60 (see block 62). The carrier member 18 adheres to the upper surface 26 of the web roll 38, thereby sealing the adhesive strips and web roll 38 (if present) between the carrier member 18 and the release backing 24. A second die-cutter 64 of known construction die cut/kiss cuts through the carrier and web roll to the release backing, thereby defining rows of bandage strips (see block 66). Finally, as the compressed web roll 38, carrier member 18 and release backing 24 are rolled onto a spool 68, a slitter 72 slits the compressed web roll 38, carrier member 18 and release backing 24 along their longitudinal axis, thereby forming several continuous rolls of interconnected bandages 12 (see block 70). Those skilled in the art will recognize that the various stations of the apparatus may be connected to a central frame 74 or connected to several integral frames. Once a desired length of the continuous roll is rolled onto the spool 68 which rotates on a spindle, a slicer or cutter separates the roll, and the several continuous rolls are removed from the spindle.

Referring next to FIGS. 11–14, an alternate embodiment of the delivery device of the present invention is shown. The delivery device comprises a transparent carrier member 100, transparent adhesive strip 102, transparent blocking member 104, wound pad 106, release backing 108, and at least one pull tab 110. A tab 110 is positioned on at least one end of the delivery device sandwiched between the carrier member 100 and release backing 108. Alternatively, a tab 110 may be positioned on each end of the delivery device (see for comparison FIGS. 11–12 and FIGS. 13–14). The adhesive strip 102 may be constructed from thin films of suitable known construction and the carrier member and release backing may be manufactured from the materials as described above in the discussion of other embodiments of the invention. Likewise the adhesives bonded, coated, formed, or otherwise affixed to the carrier 100, and blocking member 104 may be of a low tactile adhesive formulated so that when the adhesive strip 102 is removed from the blocking member 104, the blocking member remains affixed to the carrier member 100 and the adhesive remains on the blocking member 104. Without any limitation intended, the adhesives may be selected from a group of nontransferable light tack adhesives commonly known in the industry as high tack/low tack adhesive, available from Minnesota Mining and Manufacturing, Inc., St. Paul, Minn. Further, the blocking member 104 is preferably manufactured from a multi-layer polyethylene film of known suitable construction and having the low tactile adhesive layer formed on at least one planar surface thereof. The blocking member or film 104 is stiffer than the films used to form the carrier member 100 and release backing 108 whereby the stiffer blocking film prevents curling and assists in retaining a planar shape of the delivery device. Those skilled in the art will appreciate that the blocking member may be eliminated when the adhesive strip 102 is constructed from a more rigid film such as vinyl, for example.

During the manufacture of a continuous roll of delivery devices, wound pads 106 are selectively placed on a continuous roll of thin film suitable for use as the adhesive strip 102. A continuous roll of the blocking film 104 is positioned over an upper surface of the continuous roll of adhesive strips 102. Then a continuous roll of release backing 108 is positioned against the lower surface of the continuous roll of adhesive strips 102. A die cut/kiss cut is then made through the blocking film 104 and adhesive film 102. The die may be formed in any of a variety of desired shapes. The outer frame of the blocking film and adhesive film are stripped away and a continuous roll of carrier film 100 is positioned over the top of the cut out blocking members 104 and adhesive strips 102 (see FIG. 18). The carrier film is die cut at preselected intervals to thereby define the length of the bandage or strip. Of course, the cut may extend through all the layers of film to thereby create a plurality of individual delivery devices. The continuous carrier 100 and release backing 108 may then be rolled onto a spindle to form a continuous roll of sterile delivery devices.

Figure 16:
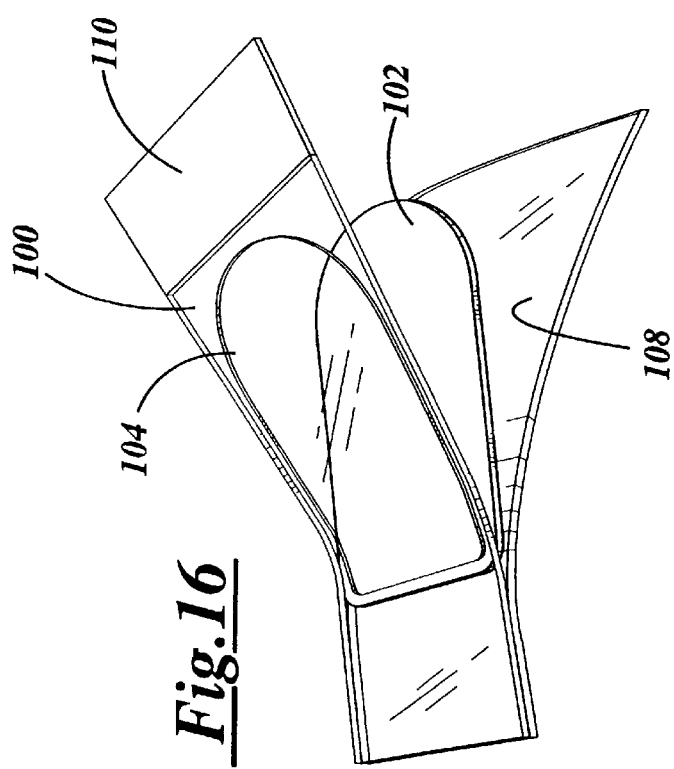
FIG. 16 is a perspective view of an individually packaged adhesive thin film or strip having the release backing and carrier member partially separated for clarity.
Figure 17:
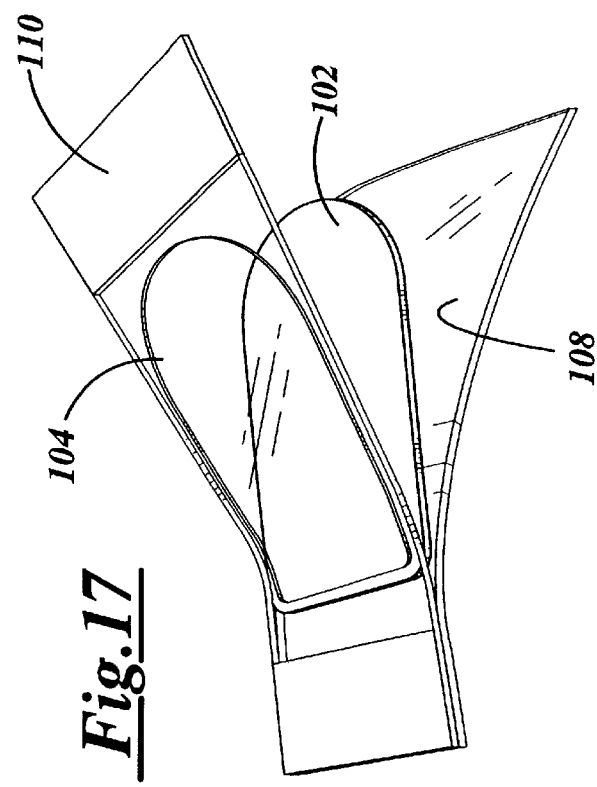
FIG. 17 is a perspective view of an individually packaged bandage having the release backing and carrier member partially separated for clarity.

FIGS. 15–17 illustrate the delivery device constructed from thin films having the wound pad removed. Without any limitation intended, the thin films may be transparent to allow the user to center the adhesive strip over the desired location. Applying the adhesive strip to a desired location with a certain degree of precision may prove advantageous in certain applications. For example, the delivery device may be used to securely hold an intravenous (IV) needle and tube against the wrist, whereby centering the needle under the strip may be desirable. The transparent adhesive strip provides a see-through hold down, while isolating the IV needle from potential contaminating contacts with external contaminants.

Figure 20:
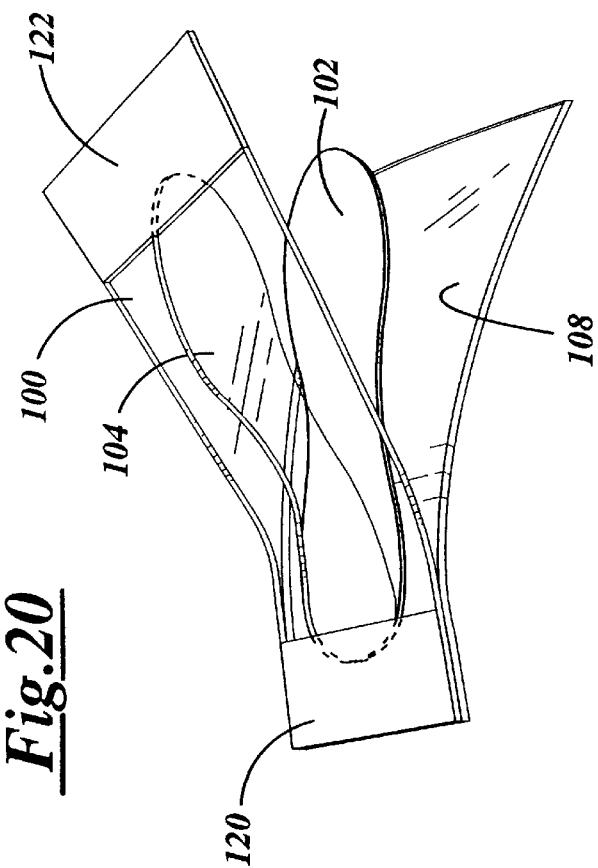
FIG. 20 is a top plan view of the bandage of the type shown in FIG. 19.
Figure 19:
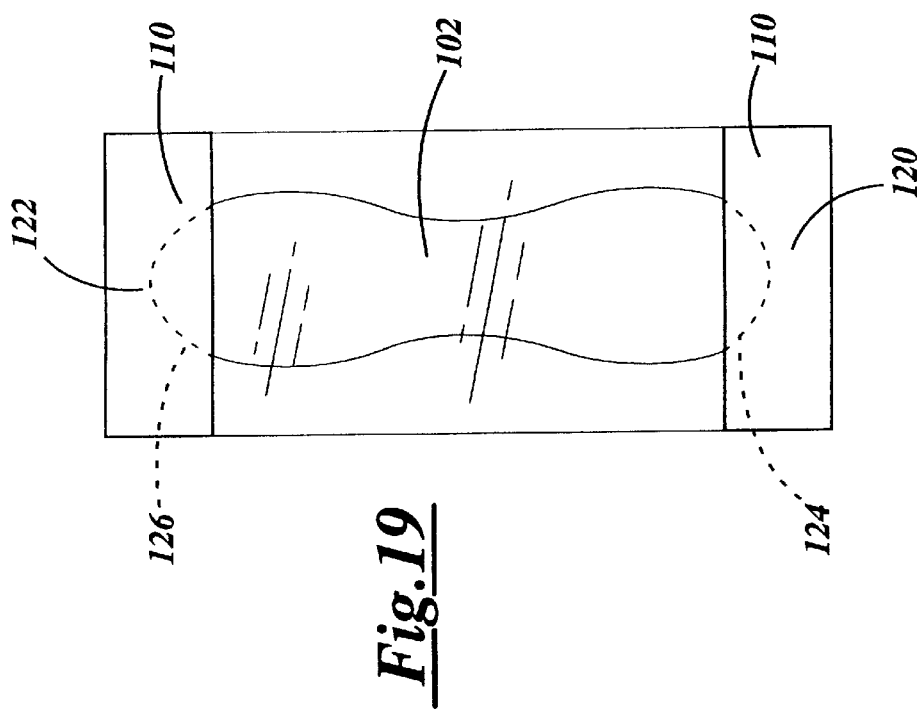
FIG. 19 is a perspective view an individually packaged bandage or strip having the release backing and carrier member partially separated for clarity.

Referring now to FIGS. 19–20 another alternate embodiment of the sterile delivery device is shown. The adhesive bandage 102 is formed from vinyl, woven fabric, non-woven fabric, polyester or other material suitable for use as an adhesive bandage, wherein the bandage 102 has an adhesive coated on the bottom surface thereof. The bandage 102 is sandwiched between the carrier member 100 and release backing 108, wherein a low tactile adhesive is coated on the lower planar surface of the carrier member 100. First tab 120 is attached to one end of the carrier member 100 and second tab 122 is attached to the opposite end of the carrier member 100. The ends or tips 124 and 126 of the bandage 102 overlap with the respective tabs 120 and 122. Alternatively, it may be desirable that only tip 124 overlap with tab 120. An adhesive is applied to tab 120, wherein the overlapping portion of tip 124 adheres to the tab 120. Thus, the carrier member and adhesive portion of the tab overlap the upper surface of the bandage. In use, the user pulls on tab 120, thereby separating the carrier member 100 and bandage 102 from the release backing 108. The difference in tactile between the adhesive on the carrier member 100, tab 120, and strip 102 allows the strip 102 to separate from the release backing 108 while adhering to the carrier member 100 and tab 120. Then the user applies the bandage to a desired surface, pressing against the upper surface of the carrier member 100. Once the bandage is in place, the user then pulls on tab 122 to thereby peel the carrier member 100 and tab 120 from the bandage 102. In this manner, the need for a blocking member is eliminated. Those skilled in the art will appreciate that some form of indicia, for example color coding, may be applied to tabs 120 and 122, wherein the color coding may be utilized by the user to identify the proper sequence of pulling on the tabs. Of course a dispenser may be utilized such that the user must inherently first pull on tab 120 to separate the bandage and carrier member from the release backing. One such dispenser is disclosed in co-pending application filed by the same inventor concurrently with the present application, the entire disclosure of which is incorporated herein by reference for any purpose.

This invention has been described herein in considerable detail in order to comply with the patent statutes and to provide those skilled in the art with the information needed to apply the novel principles and to construct and use such specialized components as are required. However, it is to be understood that the invention can be carried out by specifically different devices, and that various modifications, both as to the equipment details and operating procedures, can be accomplished without departing from the scope of the invention itself.

What is claimed is:

1. A delivery device including a sterile element that may be removed from its sealed enclosure without contaminating any portion of the element, said device comprising:

(a) a strip being die cut to define a shape of the element;

(b) a blocking member congruent with said strip and attached to an upper planar surface of said strip;

(c) a removable carrier member attached to an upper planar surface of said blocking member, wherein said carrier member overlaps the upper planar surface of said blocking member;

(d) a pull tab associated with a lower planar surface of said carrier member; and (e) a removable release backing engaged with a lower planar surface of said strip, wherein said release backing overlaps the lower planar surface of said strip, thereby isolating said strip, blocking member and tab between said release backing and said carrier member.

2. The device as recited in claim 1, wherein the carrier member has a light tack adhesive coating deposited on a lower strip engaging surface of said carrier member.

3. The device as recited in claim 1, wherein the strip has an adhesive coating deposited on the lower planar surface of said strip.

4. The device as recited in claim 3, further including a wound pad attached to the lower planar surface of said strip, wherein said wound pad is centered on the lower planar surface of said strip.

5. The device as recited in claim 1, wherein said blocking member includes a light tack adhesive coating deposited on a lower planar surface of said blocking member.

6. The device as recited in claim 1, further including a removal tab attached to the lower planar surface of said carrier member, wherein said pull tab and said removal tab are spaced apart such that a major portion of the strip is positioned therebetween.

7. The device as recited in claim 6, wherein a tip of said strip engages a portion of a lower planar surface of said pull tab, said portion of the lower planar surface of said pull tab having an adhesive deposited thereto.

8. The device as recited in claim 1, wherein said strip is manufactured from a material selected from the group consisting of vinyl, woven fabric, non-woven fabric, and polyester.

9. The device as recited in claim 1, wherein said strip is manufactured from a material selected from the group consisting of a thin film, urethane, and polyurethane.

10. The device as recited in claim 8, further including a removal tab attached to the lower planar surface of said carrier member, wherein said pull tab and said removal tab are spaced apart such that a major portion of the strip is positioned therebetween.

11. The device as recited in claim 10, wherein a tip of said strip engages a portion of a lower planar surface of said pull tab, said portion of the lower planar surface of said pull tab having an adhesive deposited thereto.

12. A delivery device including a sterile strip that may be removed from its sealed enclosure without contaminating any portion of the strip, said device comprising:

(a) a strip being die cut to define a shape of the strip;

(b) a blocking member, said backing member being substantially congruent with said strip and attached to an upper planar surface of said strip;

(c) a removable carrier member attached to an upper planar surface of said blocking member, wherein said carrier member overlaps the upper planar surface of said blocking member;

(d) a pull tab attached to a lower planar surface of said carrier member, said pull tab having an adhesive deposited on a portion of a lower planar surface of said pull tab, wherein a tip of said strip engages a portion of a lower planar surface of said pull tab; and (e) a removable release backing engaged with a lower planar surface of said strip, wherein said release backing overlaps the lower planar surface of said strip, thereby isolating said strip and said tab between said release backing and said carrier member.

13. The device as recited in claim 12, wherein the carrier member has a light tack adhesive coating deposited on a lower strip engaging surface of said carrier member.

14. The device as recited in claim 12, wherein the strip has an adhesive coating deposited on the lower planar surface of said strip.

15. The device as recited in claim 14, wherein a wound pad is attached and centered on the lower planar surface of said strip.

16. The device as recited in claim 12, wherein said blocking member includes a light tack adhesive coating deposited on a lower planar surface of said blocking member.

17. The device as recited in claim 12, wherein said strip is manufactured from a material selected from the group consisting of a thin film, urethane, and polyurethane.

18. The device as recited in claim 12, further including a removal tab attached to the lower planar surface of said carrier member, wherein said pull tab and said removal tab are spaced apart such that a major portion of the strip is positioned therebetween.

19. The device as recited in claim 12, wherein a plurality of strips are aligned and attached in series to a continuous roll of release backing.

20. The device as recited in claim 12, wherein said carrier member is manufactured from a transparent material.

21. The device as recited in claim 12, wherein said strip is manufactured from a material selected from the group consisting of vinyl, woven fabric, non-woven fabric, thin film, urethane, and polyester.

22. The device as recited in claim 21, further including a removal tab attached to the lower planar surface of said carrier member, wherein said pull tab and said removal tab are spaced apart such that a major portion of the strip is positioned therebetween.

* * * * *